United States Patent
Beauchamp et al.

(10) Patent No.: US 11,235,152 B2
(45) Date of Patent: Feb. 1, 2022

(54) SYSTEMS AND METHODS OF CONVEYING A VISUAL IMAGE TO A PERSON FITTED WITH A VISUAL PROSTHESIS

(71) Applicant: Baylor College of Medicine, Houston, TX (US)

(72) Inventors: Michael S. Beauchamp, Houston, TX (US); Daniel Yoshor, Houston, TX (US); William H. Bosking, III, Austin, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 16/970,804

(22) PCT Filed: Mar. 5, 2019

(86) PCT No.: PCT/US2019/020649
§ 371 (c)(1),
(2) Date: Aug. 18, 2020

(87) PCT Pub. No.: WO2019/173265
PCT Pub. Date: Sep. 12, 2019

(65) Prior Publication Data
US 2021/0093864 A1     Apr. 1, 2021

Related U.S. Application Data

(60) Provisional application No. 62/638,365, filed on Mar. 5, 2018.

(51) Int. Cl.
*A61N 1/36* (2006.01)
*A61N 1/05* (2006.01)
*A61N 1/378* (2006.01)

(52) U.S. Cl.
CPC ....... *A61N 1/36046* (2013.01); *A61N 1/0543* (2013.01); *A61N 1/36167* (2013.01); *A61N 1/3787* (2013.01)

(58) Field of Classification Search
CPC ............ A61N 1/36046; A61N 1/36167; A61N 1/0543; A61N 1/3787; A61N 1/36
See application file for complete search history.

(56) References Cited

U.S. PATENT DOCUMENTS

| 2006/0167528 | A1 | 7/2006 | Roy et al. |
| 2013/0035742 | A1 | 2/2013 | Talbot et al. |
| 2013/0066397 | A1* | 3/2013 | Shivdasani .......... G09B 21/008 607/53 |

FOREIGN PATENT DOCUMENTS

| EP | 2512373 A1 | 10/2012 |
| WO | 2016044296 A1 | 3/2016 |

OTHER PUBLICATIONS

International Search Report and Written Opinion, International Patent Application No. PCT/US2019/020649, dated May 23, 2019.
(Continued)

*Primary Examiner* — Eugene T Wu
(74) *Attorney, Agent, or Firm* — Saul Ewing Arnstein & Lehr LLP; Kathryn Doyle; Brian R. Landry

(57) ABSTRACT

One aspect of the invention provides a computer-implemented method of conveying a visual image to a blind subject fitted with a visual prosthesis. The computer-implemented method includes: mapping a representation of a visual image onto a two-dimensional array of points having a resolution greater than or equal to an electrode resolution of the visual prosthesis; identifying one or more continuous paths along the mapped representation; and controlling the visual prosthesis to sequentially actuate electrodes along the one or more paths. Another aspect of the invention provides a system including: a visual prosthesis comprising multiple
(Continued)

A    Existing VCPs

B    Dynamic current steering electrodes; and an imaging processing device in communication with the visual prosthesis. The imaging processing device can be programmed to receive an image and perform any of the methods described herein.

12 Claims, 12 Drawing Sheets

(56) References Cited

OTHER PUBLICATIONS

MathWorks, "Edge detection methods for finding object boundaries in images", https://www.mathworks.com/discovery/edge-detection.html, downloaded Feb. 14, 2018.
Wikipedia, "Edge detection", https://en.wikipedia.org/wiki/Edge_detection, downloaded Feb. 14, 2018, 10 pages.
Argall, B. D., et al., "Simplified Intersubject Averaging on the Cortical Surface Using SUMA", Human Brain Mapping 27, 2006, 14-27.
Beauchamp, M. S., et al., "Dynamic Electrical Stimulation of Sites in Visual Cortex Produces Form Vision in Sighted and Blind Humans", bioRxiv, Nov. 5, 2018, 24 pages.
Bosking, W. H., et al., "Rules Governing Perception of Multiple Phosphenes by Human Observers", bioRxiv, Apr. 17, 2018, 31 pages.
Bosking, W. H., et al., "Saturation in phosphene size with increasing current levels delivered to human visual cortex", JNeurosci, Jun. 26, 2017, 47 pages.
Grigoryev, A., et al., "Vision-based Vehicle Wheel Detector And Axle Counter", Proceedings 29th European Conference on Modelling and Simulation, May 29, 2015, 6 pages.
Murphey, D. K., et al., "Perceiving electrical stimulation of identified human visual areas", PNAS: 106(13), Mar. 31, 2009, 5389-5393.
Yoshor, D., et al., "Receptive Fields in Human Visual Cortex Mapped with Surface Electrodes", Cerebral Cortex 17:, Oct. 2007, 2293-2302.
Communication, Extended European Search Report, European Patent Application No. 19764847.0, dated Oct. 11, 2021.

* cited by examiner

SYSTEMS AND METHODS OF CONVEYING A VISUAL IMAGE TO A PERSON FITTED WITH A VISUAL PROSTHESIS

CROSS-REFERENCE TO RELATED APPLICATIONS

This application is a national phase application under 35 U.S.C. 371 of International Application No. PCT/US2019/020649, filed Mar. 5, 2019, which claims the benefit of priority to U.S. Provisional Patent Application Ser. No. 62/638,365, filed Mar. 5, 2018. The entire content of each application is hereby incorporated by reference herein.

STATEMENT REGARDING FEDERALLY SPONSORED RESEARCH OR DEVELOPMENT

This invention was made with government support under Contract No. NIH 5R01EY023336 awarded by the National Institutes of Health. The government has certain rights in the invention.

BACKGROUND OF THE INVENTION

Advances in technology have recently spurred at least four different research groups to seek approval for clinical trials of new visual cortical prosthetics (VCPs) that restore vision to the blind. All VCPs rely on electrical stimulation of visual cortex to produce percepts of spots of lights, known as phosphenes, even in patients who have been blind for many years. A wearable camera captures the visual scene and a pattern of phosphenes that approximates the scene is produced by electrically stimulating visual cortex, bypassing irreparably damaged eyes and optic nerves. A key assumption is that patients will integrate the pattern of phosphenes into a useable image, like pixels in a visual display.

SUMMARY OF THE INVENTION

One aspect of the invention provides a computer-implemented method of conveying a visual image to a blind subject fitted with a visual prosthesis. The computer-implemented method includes: mapping a representation of a visual image onto a two-dimensional array of points having a resolution greater than or equal to an electrode resolution of the visual prosthesis; identifying one or more continuous paths along the mapped representation; and controlling the visual prosthesis to sequentially actuate electrodes along the one or more paths.

This aspect of the invention can have a variety of embodiments. The resolution of the two-dimensional array of points can be greater than the electrode resolution of the visual cortical prosthetic and the controlling step can further include simultaneously actuating electrodes to localize a signal to a spatial point intermediate to the simultaneously actuated electrodes. The simultaneously actuated electrodes can receive identical current levels and spatial location of the percept is about halfway between the electrodes. The simultaneously actuated electrodes can receive different current levels and distances between spatial location of the percept and the electrodes are proportional to a ratio of current levels applied to the electrodes.

The visual cortical prosthetic can be controlled to sequentially actuate the plurality of electrodes at a rate between about 2 times per second and 100 times per second. The electrodes can be actuated for a duration between about 10 ms and about 500 ms.

The controlling step can further include applying an interstimulation gap between each sequential actuation. The interstimulation gap can be between about 0 ms and about 100 ms.

The representation can include one or more graphemes.

The representation of the visual image can be derived from a video image capture.

Another aspect of the invention provides a system including: a visual prosthesis comprising multiple electrodes; and an imaging processing device in communication with the visual prosthesis. The imaging processing device can be programmed to receive an image and perform any of the methods described herein.

This aspect of the invention can have a variety of embodiments. The visual prosthesis can be selected from the group consisting of: a visual cortical prosthesis and a retinal prosthesis.

BRIEF DESCRIPTION OF THE DRAWINGS

For a fuller understanding of the nature and desired objects of the present invention, reference is made to the following detailed description taken in conjunction with the accompanying drawing FIG.s wherein like reference characters denote corresponding parts throughout the several views.

DEFINITIONS

Figure 1:
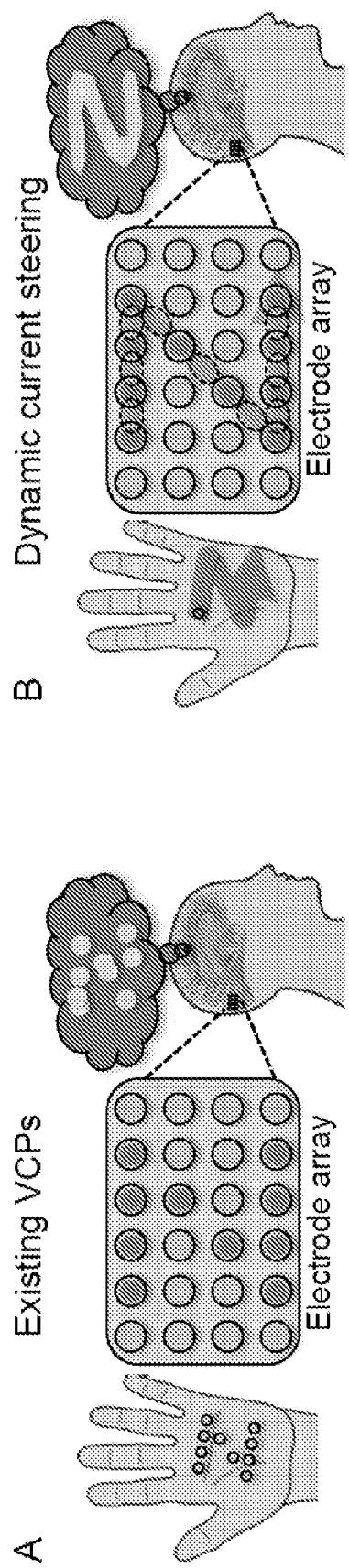
FIG. 1 depicts dynamic current steering according to an embodiment of the invention. In Panel A, the shape of a "Z" is presented by pressing multiple points into the palm of the hand. Analogously, existing VCPs simultaneously stimulate multiple electrodes (red circles, which appear as dark circles in grayscale). In both cases, subjects perceive only a disconnected set of points (thought bubble). In Panel B, the "Z" shape is presented by tracing a single point across the palm. Analogously, in dynamic current steering, real and virtual electrodes (dashed red/dark circles) are stimulated in sequence, resulting in a coherent percept.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Unlike pixels, multiple phosphenes are not easily combined into a percept of a coherent form. Despite numerous attempts, Applicant did not find that a coherent spatial form is perceived when more than one electrode is stimulated to form a pattern. Instead of a unified form, subjects reported seeing a series of discrete dots or blobs that are centered on or near the RF of each electrode stimulated. This raises the uncomfortable possibility that clinical trials of new VCPs will result in patients who see an array of disconnected points of light instead of visual forms: a serious setback.

Embodiments of the invention provide a novel stimulation paradigm, termed "dynamic current steering," that promises to dramatically enhance the ability of VCPs to produce useful percepts of visual forms. Dynamic current steering can include two components.

The "dynamic stimulation" component refers to rapidly sweeping electrical stimulation across the retinotopic map in a pattern that corresponds to the desired visual object. This dynamic sweeping combines the individual phosphenes into a unified percept. The somatosensory system provides a useful analogy: to convey a specific letter, such as "Z", through touch, one could either press a "Z" shape consisting of multiple individual points into the hand (the conventional approach) or one could trace a "Z" across the hand using a single point (the dynamic approach).

The "current steering" component refers to concurrently stimulating nearby electrodes to produce activation at a location in between the electrodes. This is helpful because existing electrode arrays are not dense enough for dynamic stimulation to stimulate every desired location in cortex. Current steering enables virtual electrodes that approximate a continuous trajectory.

Without being bound by theory, Applicant believes, supported by preliminary data, that dynamic current steering is considerably more effective than existing VCP stimulation paradigms.

In preliminary experiments, Applicant found that stimulation of visual cortex with dynamic current steering enables patients to readily describe and even draw intended shapes with little effort or training.

Applicant has found that phosphene location could be reliably predicted based on the receptive field properties of the stimulated site, and that phosphene size could be predicted based on a combination of the current amplitude used for electrical stimulation and the location of the electrode in the map of visual space. Building on these findings, Applicant created and validated a model that accurately predicts the spatial properties of single phosphenes.

Figure 8:
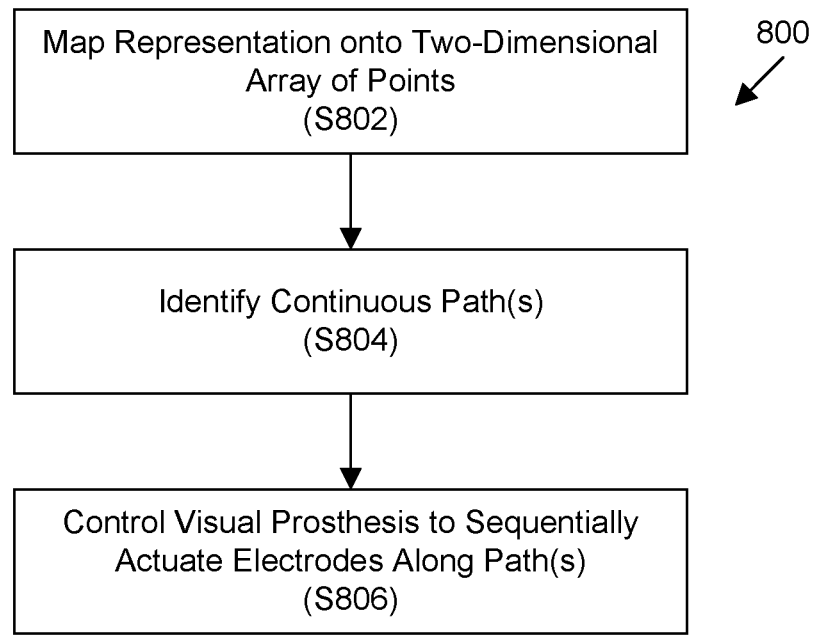
FIG. 8 depicts a computer-implemented method 800 of conveying a visual image to a blind subject fitted with a visual prosthesis according to an embodiment of the invention.

FIG. 8 depicts a computer-implemented method 800 of conveying a visual image to a blind subject fitted with a visual prosthesis according to an embodiment of the invention.

The visual prosthesis can be a device capable of producing a phosphene such as a visual cortical prosthesis or a retinal prosthesis. Exemplary visual cortical prosthetics are available from Second Sight Medical Products, Inc. of Sylmar, Calif. and described in U.S. Patent Application Publication No. 2017/0165476. One such device includes a camera, a video processing unit, an external coil, and implanted internal coil in communication with an electrode array.

In step S802, a representation of a visual image is mapped onto a two-dimensional array of points having a resolution greater than or equal to an electrode resolution of the visual prosthesis.

The visual image can be captured by an imaging device such as a camera, a video camera, a digital camera, a charge-coupled device (CCD), a complementary metal oxide semiconductor (CMOS) image sensor, and the like. For example, a video frame can be isolated from a video stream. In one embodiment, the imaging device is worn by the user to capture the user's surroundings, e.g., in real-time.

The representation of the visual image can be generated using machine vision and edge-detection techniques such as the Sobel, Canny, Prewitt, Roberts, and fuzzy logic edge-detection methods, which can be implemented in software such as MATLAB® software available from The MathWorks, Inc. of Natick, Mass. The representation of the visual image can be a black-and-white or bichromatic image.

The representation of the visual image can also be one or more graphemes such as alphabetic letters, typographic ligatures, Chinese characters, numerical digits, punctuation marks, and other individual symbols. The representation of visual images can also include shapes, emojis, and the like.

The representation of the visual image can be mapped onto the two-dimensional array using raster image scaling algorithms.

In step S804, one or more continuous paths along the mapped representation are identified.

In step S806, a visual prosthesis can be controlled to sequentially actuate a plurality of electrodes along the one or more paths. For example, a series of instructions can be provided to cause the visual prosthesis to actuate one or more electrodes over a time sequence. Using FIG. 1, Panel B as an example with a 25 ms actuation duration and a 25 ms interstimulation gap, the following series of instructions can be provided to the visual prosthesis:

TABLE 1

Exemplary Actuation Sequence

| Time | Electrodes |
|---|---|
| 0 ms | (3, 1) |
| 50 ms | (3, 1) & (3, 2) |
| 100 ms | (3, 2) |
| 150 ms | (3, 2) & (3, 3) |
| 200 ms | (3, 3) |
| 250 ms | (3, 3) & (3, 4) |
| 300 ms | (3, 4) |
| 350 ms | (3, 4) & (2, 3) |
| 400 ms | (2, 3) |
| 450 ms | (2, 3) & (1, 2) |
| 500 ms | (1, 2) |
| 550 ms | (1, 2) & (0, 1) |
| 600 ms | (0, 1) |
| 650 ms | (0, 1) & (0, 2) |
| 700 ms | (0, 2) |
| 750 ms | (0, 2) & (0, 3) |
| 800 ms | (0, 3) |
| 850 ms | (0, 3) & (0, 4) |
| 900 ms | (0, 4) |

As seen in FIG. 1, Panel B, multiple electrodes can be activated simultaneous to produce a phosphene that appear intermediate to the plurality of electrodes (the intermediate phosphene represented by lighter shading).

Figure 9:
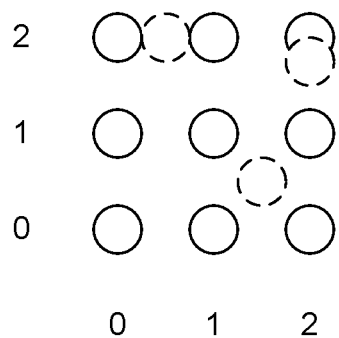
FIG. 9 depicts the localization of signals to spatial points intermediate to the plurality of simultaneously actuated electrodes according to an embodiment of the invention.

This concept is further depicted in FIG. 9, where the dashed phosphene having coordinates (0.5, 2) can be produced by activating electrodes (0, 2) and (1, 2). Similarly, the dashed phosphene having coordinates (1.5, 0.5) can be produced by activating electrodes (1, 0), (2, 0), (1, 1), and (2, 1). Intermediate phosphenes can be shifted in a desired direction by applying uneven current levels to electrodes, e.g., uneven current levels that are proportional to the desired distances between activated electrodes. For example, the dashed phosphene having coordinates (2, 1.75) can be produced by activating electrodes (2, 1) and (2, 2) with currents having a 1:3 ratio.

Prophetic Example

General Methods

The proposed study builds on Applicant's extensive experience studying human visual perception by recording from and stimulating cortical surface electrodes implanted on the occipital lobe of patients undergoing clinical evaluations for characterization of epilepsy. To minimize the possibility that brain abnormalities related to the underlying epilepsy will confound the collected data, patients are screened to exclude subjects with visual field deficits or abnormal visual processing, and data from cases where the occipital lobe is deemed to be epileptic or structurally or functionally abnormal is excluded.

Figure 3:
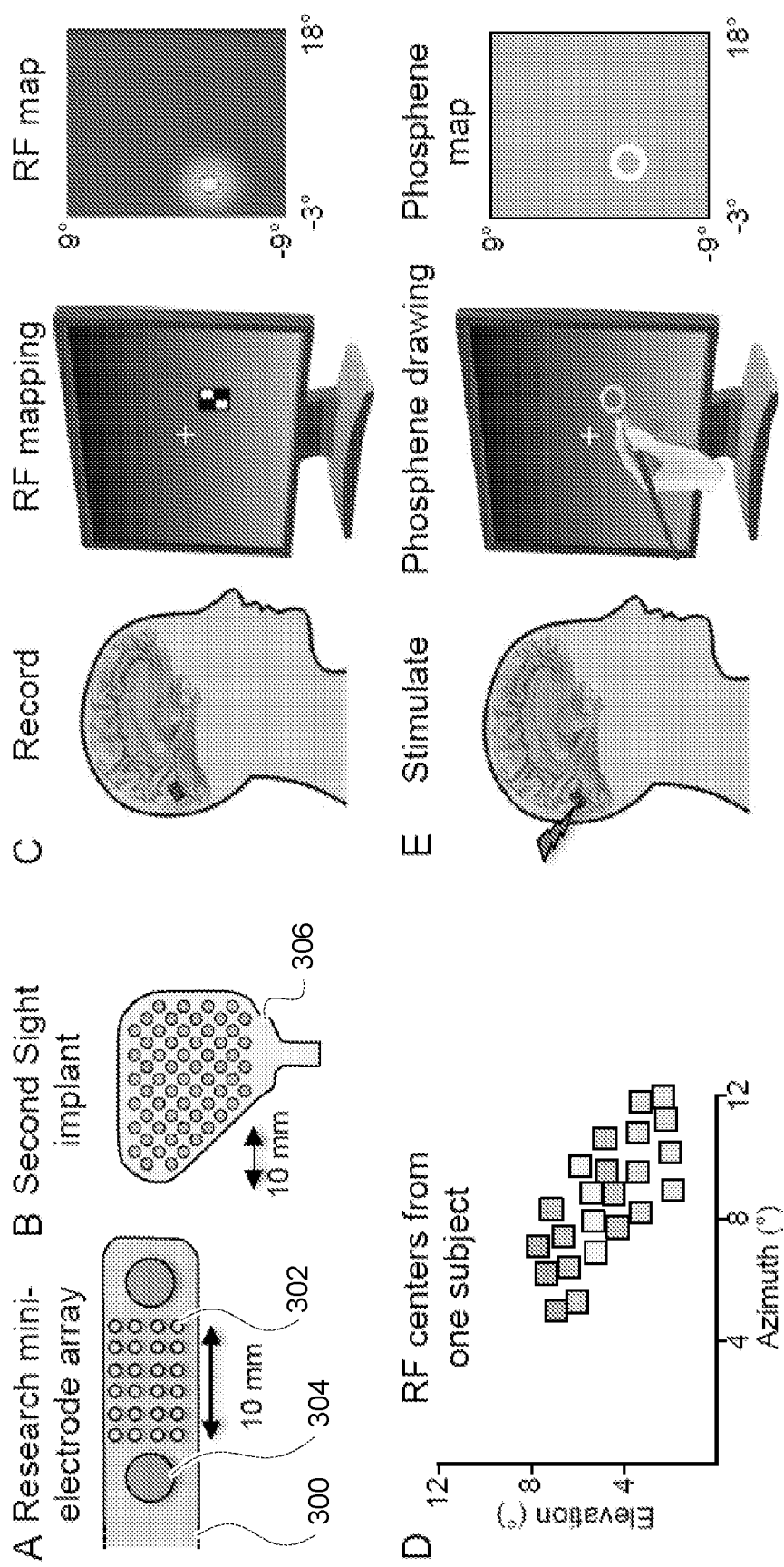
FIG. 3 depicts methods for human visual cortex recording and stimulation according to embodiments of the invention. Panel A depicts a hybrid electrode design with 24 miniature research electrodes (small gray circles) 302 located between larger clinical electrodes (large gray circles) 304 at the tip of the electrode strip 300. (Other clinical electrodes on the strip not shown.) Panel B depicts an electrode design for a SECOND SIGHT® FDA-approved implant available from Second Sight Medical Products, Inc. of Sylmar, Calif. Panel C depicts a method for mapping Receptive Fields (RFs). Subjects perform a letter-detection task at a central fixation point while checkerboard stimuli are flashed in various positions on the screen. Brain responses are recorded from each electrode and the spatial layout of the RF quantified with a Gaussian distribution. Panel D depicts RF centers obtained from the research electrodes in a recent patient. (Each color corresponds to a different column of electrodes). In Panel E, subjects fixate while electrical stimulation is delivered and then draw the outline of the phosphene they perceived on a touchscreen. An ellipse is fit to the drawing for quantification.

All experiments will be conducted with custom clinical-research hybrid electrode strips 300 (FIG. 3, Panel A; PMT Corporation, Chanhassen, Minn.). This hybrid strip 300 includes a 4×6 array of miniature (0.5 mm diameter) research electrodes 302 spaced 2 mm apart and located in the normally empty space between two standard (3 mm diameter) clinical electrodes 304. These research electrodes will be used for all of the proposed experiments, and are a reasonable proxy for the electrodes in the only FDA-approved VCP, the SECOND SIGHT® device 306 (compare FIG. 3, Panels A B). The 4×6 array allows for the creation of 24 distinct phosphenes within a small area of visual cortex (0.6 cm×1 cm). FIG. 3, Panel C shows preliminary data from a recent patient implanted with this 4×6 array on the inferior bank of the left calcarine sulcus. Using the RF mapping methods shown in FIG. 3, Panel D and further described in Yoshor et al., "Receptive Fields in Human Visual Cortex Mapped with Surface Electrodes", 17 Cerebral Cortex 2293-2302 (2016), Applicant obtained robust receptive fields (RFs) for 23 of the 24 electrodes, with RFs arranged in a highly orderly fashion in the upper right visual quadrant. The precision of this RF mapping highlights the impressive potential for using a mini-electrode array for detailed recordings and patterned multi-electrode stimulation of visual cortex.

Following RF mapping, each individual visually-responsive electrode will be stimulated and the subject will draw the percept using a stylus on a touch-screen monitor. This will be repeated across several trials to confirm reliability and results will be averaged to produce a high-quality phosphene map for each electrode (FIG. 3, Panel C). Applicant will employ biphasic stimulation at a frequency of 200 Hz to produce highly reliable phosphenes. This frequency is higher than typically used in deep brain stimulation, but is matched to the high firing-rate of active V1 neurons and has proven to be highly effective, reliable, and safe. Stimulation trains will typically be of 50 ms in duration, and the minimal current that produces a repeatable phosphene will be used, typically <1 mA. Stimulation, recording, and behavioral methods are further described in Bosking et al., "Electrical Stimulation of Visual Cortex: Relevance for the Development of Visual Cortical Prosthetics", 3 *Ann. Rev. of Vision Sci.* 141-66 (Jul. 28, 2017); Bosking et al., "Saturation in phosphene size with increasing current levels delivered to human visual cortex", *J. Neurosci.* (Jun. 26, 2017) ("Bosking 2017b"); Dulay et al., "Computer-controlled electrical stimulation for quantitative mapping of human cortical function", 110(6) *J. Neurosurg.* 1300-03 (2009); and Murphey et al., "Perceiving electrical stimulation of identified human visual areas", 106 *PNAS* 5389-93 (2009).

High-resolution T1-weighted preoperative MRIs collected from each subject will be used to create cortical surface models using FreeSurfer software as described in Dale et al., "Cortical surface-based analysis. I. Segmentation and surface reconstruction", 9 *Neuroimage* 179-94 (1999); and Fischl et al., "Cortical surface-based analysis. II: Inflation, flattening, and a surface-based coordinate system", 9 *Neuroimage* 195-207 (1999). Postoperative CTs will be aligned to the pre-op MIII with a specialized processing stream using tools from the AFNI/SUMA suite to determine electrode locations on the cortical surface with precision as described in Argall et al., "Simplified intersubject averaging on the cortical surface using SUMA", 27 *Hum. Brain. Mapp.* 14-27 (2006); and Cox, "AFNI: Software for analysis and visualization of functional magnetic resonance neuroimages", 29 *Comput. Biomed. Res.* 162-73 (1996).

Aim 1: Test Dynamic Current Steering as a Novel Method for Producing Percepts of Visual Forms.

Data Collection

Figure 4:
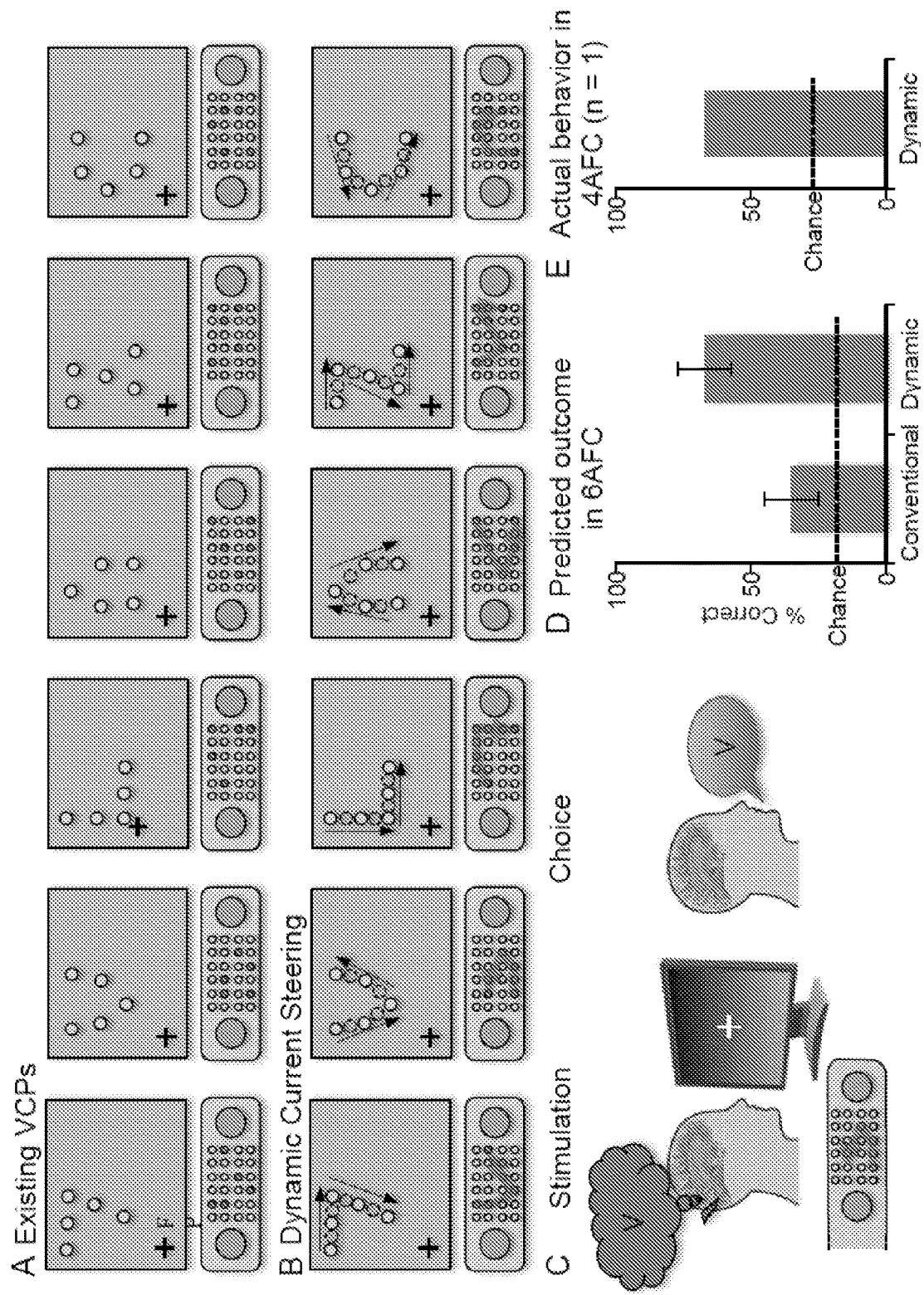
FIG. 4 compares an existing stimulation paradigm with dynamic current steering. Six different shapes are translated into stimulation patterns using the existing VCP paradigm (Panel A) or dynamic current steering (Panel B). On each trial, the brain is stimulated with one of the twelve patterns (Panel C) and the subject reports their percept. The predicted outcome is superior performance for dynamic current steering (Panel D), as supported by preliminary data (Panel E) from a recent patient.

RF and phosphene mapping will be used to identify electrodes that are visually-responsive and produce phosphenes when stimulated at low current. From this set of electrodes, Applicant will construct six spatial patterns that can be stimulated with both conventional stimulation (FIG. 4, Panel A), and dynamic current steering (FIG. 4, Panel B). Subjects will then perform a six-alternative forced choice (6-AFC) task with the patterns presented using both conventional stimulation (FIG. 4, Panel A) and dynamic current steering (FIG. 4, Panel B) in separate blocks.

In the dynamic current steering block, the stimulus duration for each real and virtual electrode will be held fixed at 50 ms and the inter-stimulus interval will also be 50 ms. Note that these parameters will be explored systematically in Aim 2. The stimulation current will be set at slightly above threshold for each of the actual electrodes. For the virtual electrode positions, the current will be set at one half of this baseline value for each electrode. Overall, during the dynamic current steering stimulation trials, there will be 450 ms of time during which one of the real or virtual electrodes is being stimulated at baseline current. During the conventional stimulation block, all five electrodes will be stimulated simultaneously for 90 ms so as to equate the total amount of stimulation per trial (current×# electrodes×time) for the two methods being tested (450 ms at 1 electrode at baseline current vs. 90 ms at 5 electrodes at baseline current). During each block there will be 72 trials (12 repetitions per pattern×6 patterns).

The spatial patterns selected for testing will be modeled after graphemes to provide a reasonable approximation to a useful visual ability, letter/number reading. To ensure that subjects do not solve the choice task using alternative strategies, all visual patterns will be presented in the same general region of visual space using as many shared phosphenes as possible. For instance, if only one of the six patterns used a peripheral phosphene, subjects could focus on only the peripheral phosphene instead of the entire pattern.

On each trial, the subject will fixate, as verified with Applicant's infrared eye tracker, while the electrical stimulation pattern is delivered. Trials with poor fixation will not be analyzed as eye movements during stimulation cause the phosphenes to shift. Subjects will indicate the perceived pattern with a verbal report (FIG. 4, Panel C). A cue screen will be presented if needed.

Preliminary Data

Figure 2:
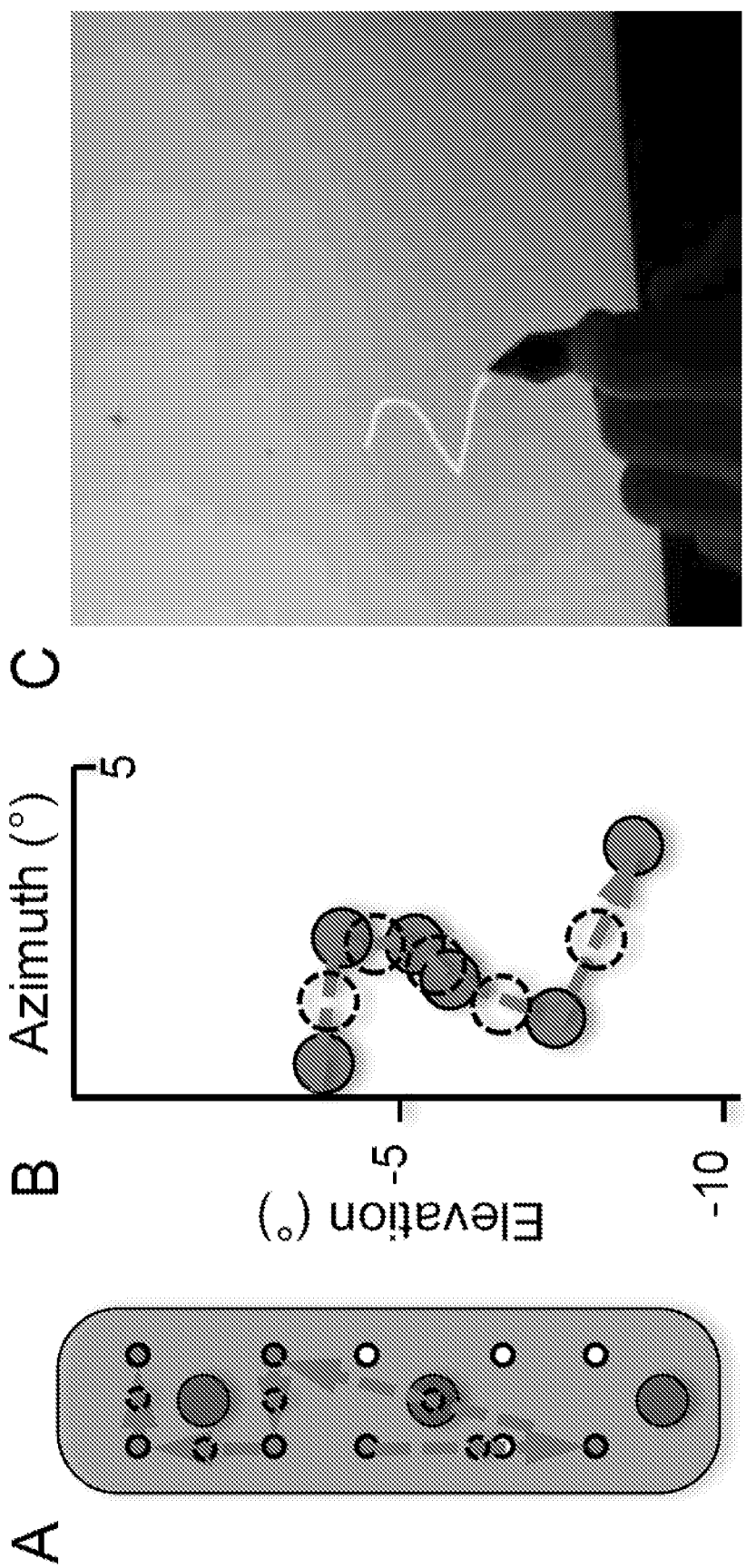
FIG. 2 depicts the effectiveness of dynamic current steering according to an embodiment of the invention. Panel A depicts an electrode array showing stimulated physical electrodes (solid red/filled small circles) and virtual electrodes (dashed red/filled circles). The red dashed arrow shows a temporal order. Panel B depicts the percept predicted by Applicant's computational model of phosphene generation, plotted in visual space. Panel C is a frame grab from a movie of the subject drawing the pattern on a touch screen following brain stimulation.

Applicant has tested dynamic stimulation in three subjects with promising results. FIG. 2 shows an example of using dynamic current steering to convey the letter "Z". In this example, the subject was implanted with an early version of our clinical-research hybrid electrode, consisting of four miniature research electrodes surrounding each of the first four clinical recording electrodes. From these research electrodes, six were selected for use in patterned stimulation. The phosphenes obtained when these six electrodes were stimulated individually were located along the path of the letter "Z" in visual space. Dynamic current steering was used to sweep stimulation across these 6 physical electrodes and 5 intermediate points (virtual electrodes). During the stimulation, a tone cued the subject to maintain fixation on a small black cross presented on the touchscreen. After the stimulation was complete, the subject used a stylus to immediately draw the pattern that they had perceived. As can be seen, the subject readily drew a pattern that corresponded to the predicted pattern, an outcome that was never achieved with simultaneous stimulation of multiple electrodes.

Data Analysis and Expected Outcomes

Percent correct in the 6AFC task will be used to compare performance with chance levels (16.7%) and to compare the effectiveness of dynamic current steering stimulation with conventional stimulation for the same patterns. Applicant predicts that the subject will be at near chance levels of performance for this task using conventional stimulation, but significantly above chance when dynamic current steering is used (FIG. 4, Panel D). This is supported by preliminary data from a recent subject who performed a 4AFC version of this task at well above chance levels using dynamic stimulation (FIG. 4, Panel E). Applicant will combine data from all subjects and test for significant differences between the dynamic current steering blocks and the conventional blocks using a Wilcoxon signed-rank test. In addition to the overall percent correct, Applicant will examine the specific errors that the subjects made by building a confusion matrix and assess discrimination performance on each of the six individual patterns.

Potential Pitfalls and Alternative Approaches

The same stimulation current delivered to different electrodes may produce phosphenes that vary in apparent brightness. If one phosphene is very bright or dim, the subject may be unable to integrate it into the overall pattern. In this case, Applicant will adjust the currents used for different electrodes so that all of the individual phosphenes appear to be of approximately the same brightness to the subject. This should often be an effective countermeasure, as current amplitude is typically correlated with phosphene intensity.

The constructed patterns could be artificially easy to distinguish if they are in very different parts of the visual field. For instance, if the electrode array spanned the calcarine sulcus, some phosphenes would be in the upper half of the visual field and some would be in the lower half. To avoid this problem, Applicant will be careful to select electrodes solely within either the upper or lower visual field for each pattern.

Aim 2: Optimize Dynamic Current Steering to Promote Perception of Coherent Forms Our preliminary data suggests that dynamic current steering will provide a significant advance over the current paradigm. The goal of Aim 2 is to optimize the individual components of dynamic current steering to provide maximum efficiency and accuracy for delivering visual forms with the final goal of implement in a VCP.

Aim 2a: Optimize Temporal Parameters for Dynamic Stimulation

Figure 5:
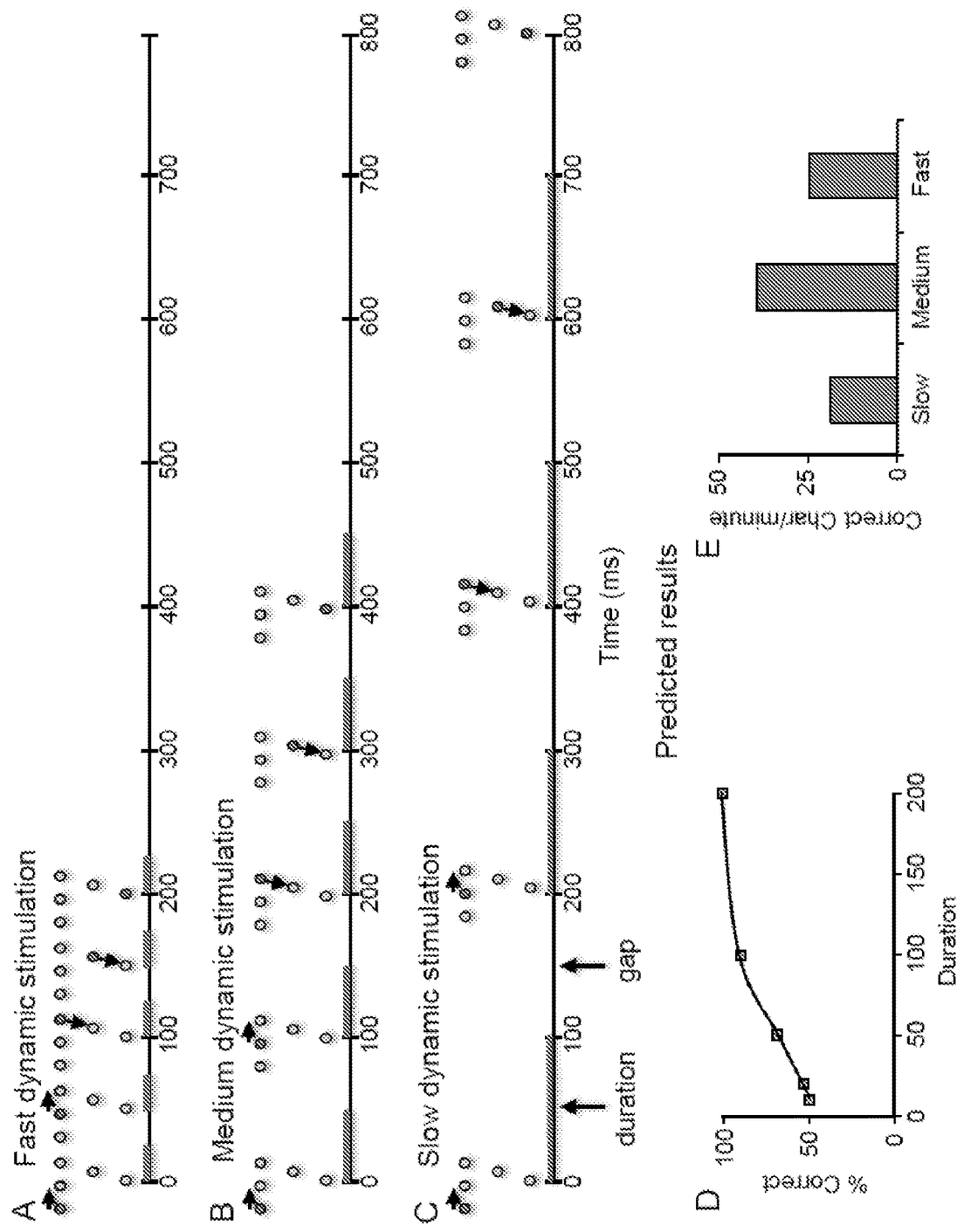
FIG. 5 depicts methods for optimizing dynamic stimulation according to an embodiment of the invention. In Panel A, a fast dynamic stimulation sequence with a stimulus duration of 25 ms (gray bar on x-axis) for each electrode and a 25 ms interstimulation interval gap between successive stimulation periods (25 ms, 25 ms). The red/dark circle indicates which electrode is stimulated at each time point. Panel B depicts a medium speed stimulation sequence (50 ms, 50 ms). Panel C depicts a slow sequence (100 ms, 100 ms). Panel D depicts a predicted psychophysical curve depicting percent correct in a 6AFC task vs. duration. Panel E depicts a predicted number of correct character discriminations per minute using the slow, medium, and fast sequences.

In Aim 2a, Applicant will use dynamic stimulation without current steering. Only physical electrodes (not virtual electrodes) will be stimulated. As shown in FIG. 5, dynamic stimulation has two main parameters: the duration of stimulation for each electrode and the inter-stimulation interval between successive electrodes. Applicant will vary both of these parameters and assess their effect on perception using three measures: (1) discrimination performance (percent correct) in a 2 AFC task, (2) a continuity index in which the subject reports the continuity or coherence of the shape they perceived, and (3) a measure of the number of characters that can be successfully discriminated per minute in a letter stream task.

Design and Data Collection

After RF mapping and screening of individual electrodes (as in Aim 1), Applicant will construct two patterns that can be used in a difficult discrimination task.

In the first experiment, the subject will perform a 2-AFC discrimination task while the duration parameter is varied across five values between 10 ms and 200 ms. (The inter-stimulation interval will be held constant at 50 ms.) Within each testing block, there will be 120 trials: five values for each stimulation duration×2 patterns×12 repetitions per condition, presented in random order. On each trial, the subject will fixate while the dynamic stimulation pattern is delivered. The subject will give an oral report to indicate which character or shape they perceived, and then the subject will give a second report indicating the continuity or coherence of the perceived shape. This index will vary from 0 (indicating no coherence, each phosphene perceived was completely independent of the others perceived), to 1 (completely continuous movement of the phosphene across the perceived shape with no obvious gaps and no independent flashing of each phosphene as it appeared). Eye movements will be monitored during the stimulation portion of the trial, and trials with large eye movements or poor fixation will be rejected.

In the second experiment, the inter-stimulation interval will be varied across five values between 0 and 200 ms while the stimulus duration is held constant at 50 ms. Within each testing block there will be 120 trials: five values for each inter-stimulation interval×2 patterns×12 repetitions per condition, presented in random order. These two experiments will allow us to construct psychometric functions (FIG. 5, Panel D) for both key parameters.

After inter-stimulation interval and duration are optimized, the third experiment will use larger character sets to determine the number of successful characters per minute that can be perceived. Subjects will perform a 6AFC task similar to the one illustrated in Aim 1 but with continuous presentation, as in an RSVP (rapid serial visual presentation) task. They will give a quick oral report of the letter or character observed as the letters are presented at a constant rate. Applicant refers to this task, which is an alternative forced choice task with a larger set of possible stimuli, as a "letter stream task". It will allow Applicant to quantify the percent correct and the number of characters per minute that the subject is able to recognize (FIG. 5, Panel E).

Data Analysis and Expected Outcomes

The experiments are designed to find the duration and inter-stimulation interval parameters that are both efficient at transmitting form information to the subject, and most effective at producing perception of coherent forms. Applicant expects that sweeping the locus of stimulation across the cortex at a moderate rate will provide for the best discrimination performance and perceived continuity of the shapes. Applicant predicts that dynamic sequences that are too fast will lead to too much bleeding together of the phosphenes produced by each electrode combination, and thus an unrecognizable form, while stimulation sequences that are too slow will be inefficient in terms of the number of characters delivered per minute, and will produce independent flashes associated with each electrode combination rather than a single coherent form.

Applicant will construct psychophysical curves that depict percent correct vs. duration (FIG. 5, Panel D) and percent correct vs. gap (not shown, but analogous to FIG. 5, Panel D). The exact form that these functions will take is not clear. For example, small gap times could lead to the best discrimination performance and perception of continuity, and performance could become progressively worse with longer times. Or, alternatively, the discrimination performance vs. gap and duration times could be maximal at intermediate levels. If appropriate, Applicant will fit a logistic function to the data, and determine the threshold duration and gap.

Aim 2b: Optimize Spatial Parameters for Current Steering

In Aim 2b, Applicant will use the optimized parameters for dynamic stimulation developed in Aim 2a without current steering and combine them with current steering, stimulating both physical and virtual electrodes. The conceptual framework underlying these experiments is the hypothesis that the phosphenes perceived by the subject are directly related to the amount and location of visual cortex that is activated above threshold.

Figure 6:
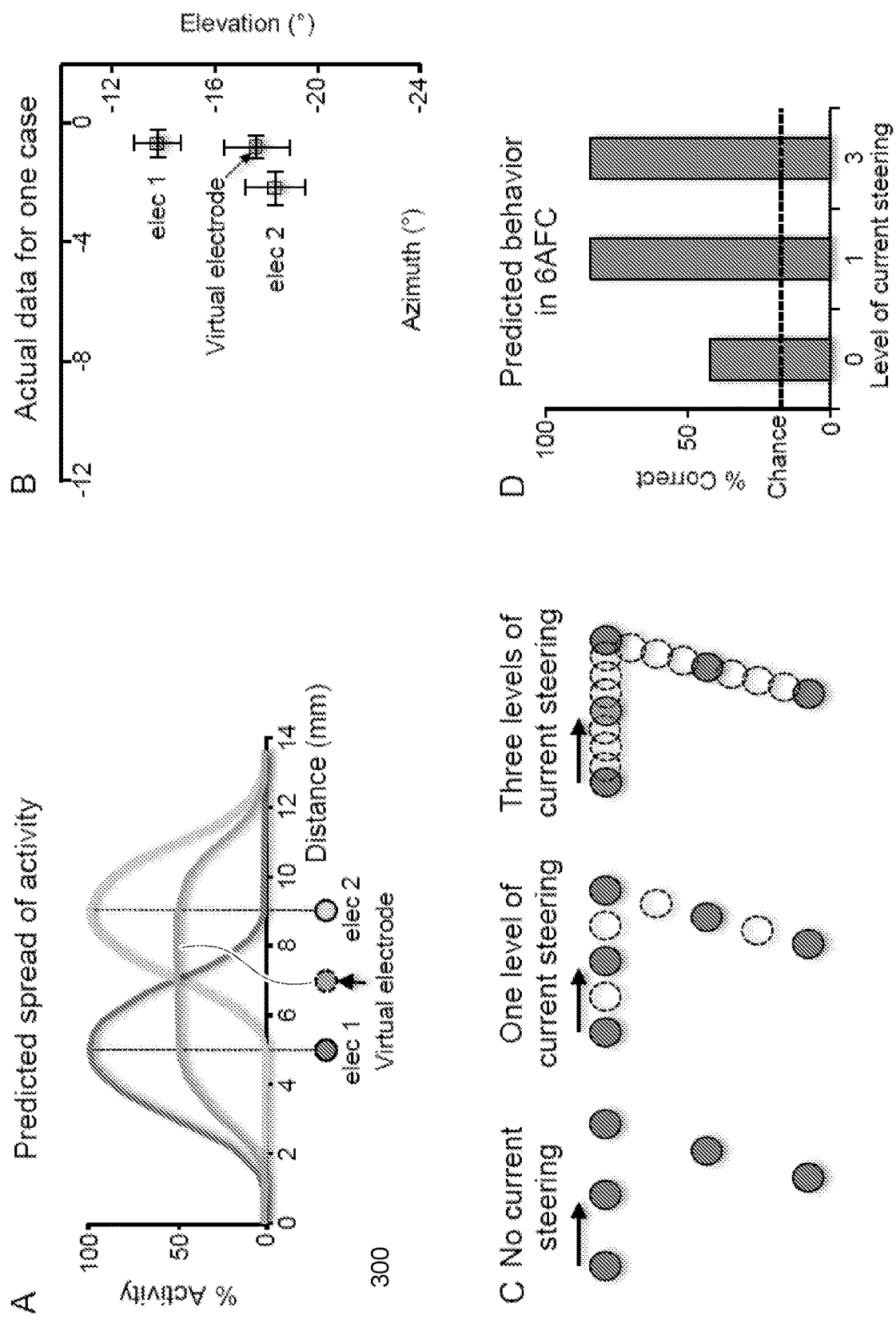
FIG. 6 depicts methods for optimizing current steering according to embodiments of the invention. Panel A depicts current steering between two physical electrodes (solid circles "elec 1" and "elec 2") separated by 4 mm. With current at 2 mA, activity spread from each electrode is expected to have a diameter of 6 mm (red and green curves). Stimulating each electrode with 1 mA is predicted to create an activity spread equivalent to stimulating a virtual electrode between the two electrodes. Panel B depicts actual data obtained from one subject where current steering was tested with two electrodes separated by 4 mm. The perceived phosphene obtained during current steering ("Virtual electrode", bars indicate standard deviation in each axis) lies between the two physical electrode phosphene locations ("elec 1" and "elec 2"). Panel C depicts current steering with 0, 1, or 3 virtual electrodes between each physical electrode. Panel D depicts a predicted impact on discrimination performance in a 6AFC task.

The basic principle of current steering is that stimulating two nearby electrodes produces a focus of neural activity that is intermediate between them (FIG. 6, Panel A).

Preliminary Data: Evidence that Current Steering Works in Visual Cortex

Preliminary data obtained from a recent patient is displayed in FIG. 6, Panel B. In this patient, Applicant tested current steering between two electrodes located 4 mm apart on one of our hybrid strips. Eight repetitions of three current ratios were tested in random order. As expected, the mean location of the phosphenes observed moved in a predictable manner, with the phosphene produced by stimulation of the located between the phosphenes produced by stimulation of the two physical electrodes.

Proposed Experiments

First, Applicant will obtain RFs and define electrodes that produce phosphenes when stimulated with low currents. Next, pairs of electrodes located 2-10 mm apart on the cortical surface will be selected. Baseline stimulation values for each electrode that are slightly above discrimination threshold, and which produce percepts of approximately the same brightness, will be determined for each electrode.

In the first set of experiments, five current ratios ranging from 100% electrode 1 to 100% electrode 2 will be tested for each pair of electrodes (E1 100%/E2 0%, E1 75%/E2 25%, E1 50%/E2 50%, E1 25%/E2 75%, and E1 0%/E2 100%; percentages refer to the percent of baseline value for each electrode). Twelve repetitions of each current ratio will be presented in random order to the subject. On each trial, the subject will fixate a small cross on a touchscreen during stimulation, and then indicate the center of the perceived phosphene using a stylus following the offset of the stimulation. (This is the same procedure utilized when the subjects draw individual phosphenes, except in this case the subject only indicates the center of the phosphene in order to save precious experimental time). As with Applicant's other proposed experiments, eye movements will be monitored during the electrical stimulating phase of the trial, and trials with large eye movements or offsets will be rejected.

In the second set of experiments, Applicant will investigate the importance of current steering for improved discrimination performance and enhancing the perception of continuous forms. Applicant will test virtual electrode numbers ranging from 0 to 3 in between each of 5 physical electrodes (FIG. 6, Panel C). Six multi-electrode patterns will be selected and the subject will perform a 6AFC task using the three levels of current steering tested in separate blocks. Trials with eye movements will be discarded.

Data Analysis and Expected Outcomes

For the first set of experiments, Applicant expects that stimulation of a virtual electrode will result in a phosphene location intermediate between that of the phosphenes produced by physical electrodes stimulation. Applicant will calculate the average location of the phosphenes plotted by the subjects for each current ratio and test for significant differences between the virtual and physical electrode locations. For the second set of experiments, Applicant predicts that current steering will improve discrimination performance and perception of continuity, but that a plateau in performance will be reached after a certain number of intermediate points (virtual electrodes) is reached. Data will be analyzed with a generalized linear mixed effects model with subject as a random factor and number of virtual electrodes (0, 1, 3 intermediate points) as a fixed factor.

Figure 7:
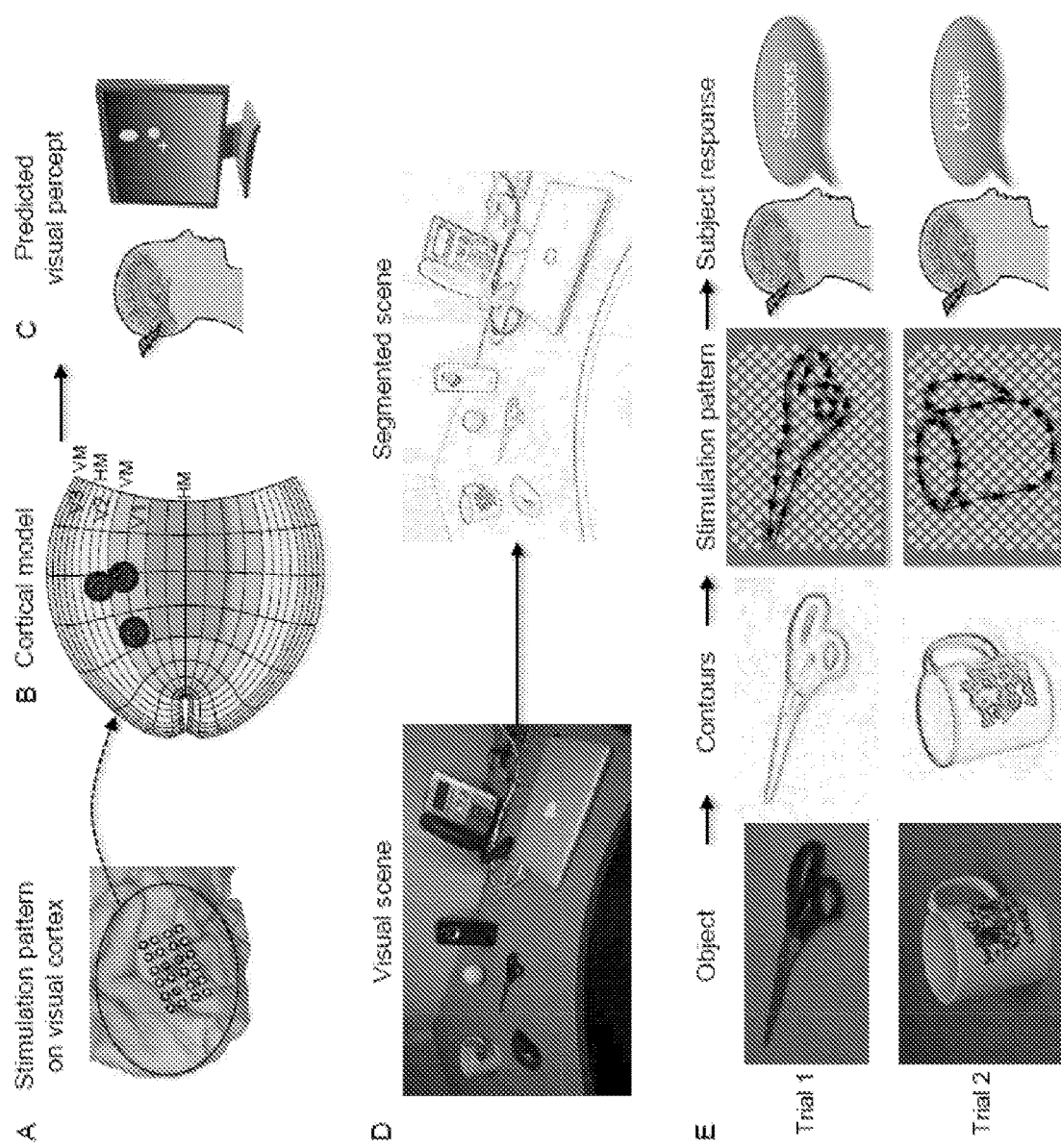
FIG. 7 depicts a model for prediction of percepts created by multi-electrode stimulation. Panel A depicts patterns of electrical stimulation using 2-6 electrodes applied to visual cortex. Panel B depicts an activity spread from each electrode is modeled using a flat map of the V1-V2-V3 complex. Panel C depicts linear summation of the activity patterns to predict the number, size, and location of phosphenes. Panel D depicts how a visual scene can be captured by a camera and object boundaries identified. In Panel E, objects presented on single trials are transformed into contours, and then into a spatial-temporal pattern of stimulation, resulting in a useful percept.

Future Directions: Model Predicting Results of Multi-Electrode Stimulation and Relevance for VCPs Applicant previously published a simple model that predicts the location and size of the phosphenes a subject will observe when single electrodes in visual cortex are stimulated in Bosking 2017b. Applicant is extending this model to predict results when two to six electrodes are stimulated simultaneously as depicted in FIG. 7, Panels A-D. For each electrode, Applicant predicts the area of cortex that will be activated above threshold. This is calculated using a variant of the activation curve described in Bosking 2017b. However, the activation area will now be assumed to be a two-dimensional Gaussian distribution, with the center of the activation over the electrode in question, and the sigma of the Gaussian distribution predicted by the activation curve as opposed to the diameter. Because the hypothesis is that spread of activity, and summation of activity, in the visual cortex will predict the number of phosphenes observed, the cortical activation predicted for each electrode is projected on to a model of the V1-V2-V3 complex (FIG. 7, Panel C). Embodiments of the invention will use linear summation of the activation patterns generated by each electrode to predict the final cortical activation pattern in response to the multi-electrode pattern. Applicant predicts that when electrodes lie close together in cortex, the activation areas from two electrodes will be highly overlapping, and this will lead to a single activation pattern when the pair is stimulated simultaneously, and thus the perception of one phosphene. When two electrodes are far apart on the cortical surface, the two activation areas should remain separate, resulting in the perception of two phosphenes.

This model can easily be extended to model more than three electrodes. As preliminary data for use in constructing this model, Applicant has data from 7 subjects using multi-electrode patterns with 2 to 6 electrodes stimulated simultaneously, including a total of 246 stimulated pairs and 67 stimulated triplets. Applicant will assess if the number, location, and size of phosphenes perceived can be predicted based on linear summation of activity in the visual cortex. If non-linear interactions are observed in the phosphene percepts, they will be added to the model.

Applicant will find the spatial and temporal parameters for dynamic current steering that will produce the most coherent visual forms for the subject. The next step will be to take these parameters and use them to create a stimulation algorithm for VCPs. This algorithm will convert arbitrary visual contours into a spatial temporal stimulation pattern that can be used to best convey the desired visual object to the subject (FIG. 7, Panels D-E). Machine vision techniques can convert real-world images into an intermediate-level representation consisting of the contours that define the borders of the object (FIG. 7, Panel D). Embodiments of the invention provides a stimulation algorithm to transform these contours into an appropriate dynamic stimulation pattern to allow the subject to perceive the desired object (FIG. 7, Panel E). This process would then be repeated for selected objects in the visual scene to allow the subject to build an internal representation of their visual surroundings.

As a first step towards this final product, Applicant will conduct more controlled experiments using a set of 10 test visual objects. Sighted epilepsy patients will be blindfolded (to approximate the experience of a blind individual) while their visual cortex is stimulated with the outlines of one of the 10 objects. The subject will give a verbal report of which object they perceived. Different objects will be presented on different trials in random order (FIG. 7, Panel E).

Following implementation of this stage in sighted epilepsy patients, Applicant will move to testing our model in blind subjects implanted with VCPs in the forthcoming clinical trials, especially the SECOND SIGHT® device. As for the sighted subjects, the blind subjects will be asked to name each of the stimulated patterns (as well as drawing it on the touchscreen).

Ultimately, there are a number of other factors that may impact the success of a VCP, including plasticity, of which Applicant's methods will allow investigation in both sighted epilepsy patients and blind VCP recipients. One key question deals with how stimulation of multiple visual areas can be integrated to form useful visual percepts. Stimulation using single electrodes is most effective in V1, V2, and V3 and stimulation of single electrodes in later areas is rarely effective. In addition, when stimulation of single electrodes leads to a percept, it is accompanied by activation of the temporal parietal junction. In sighted subjects, Applicant plans to learn what combinations of electrode stimulation, both within one cortical area and across areas, leads to activation of the TPJ and to a visual percept. Applicant may find, for example, that combinations of two or more electrodes stimulated simultaneously or combinations of electrodes stimulated using dynamic current steering are more effective at generating activation of later cortical areas and generation of a percept than activation of single electrodes alone. Another critical question is whether electrodes in multiple cortical areas can be stimulated together to generate perception of a single coherent visual form. It is often assumed that stimulation of sites in V2 and V3 on the medial wall of the occipital cortex can compensate for the lack of complete visual field coverage that results from part of V1 being buried in the calcarine sulcus. However, it has never been tested whether stimulation of electrodes in multiple cortical areas can actually lead to a single coherent visual percept.

Working Example

Materials and Methods

Subjects

The subjects for this study consisted of four sighted patients with medically intractable epilepsy (ages 20-54; all male; anonymized subject codes YBN, YAY, YBG and YBH) tested at Baylor College of Medicine (BCM) and one blind patient (age 35; female; anonymized subject code BAA) tested at University of California, Los Angeles (UCLA). All procedures were approved by the Institutional Review Boards of BCM and UCLA.

Electrodes

Subdural electrodes were implanted on the surface of the occipital lobe. In the epileptic patients, clinical electrodes were implanted for monitoring of epileptogenic activity, with electrode placement guided solely by clinical criteria. Additional research electrodes (embedded in the same silastic strips used for clinical monitoring) were implanted and stimulated for the studies described here. Clinical monitoring continued uninterrupted during experimental sessions.

For patient YBN, the research electrodes consisted of a six-by-four grid of electrodes (total of 24 electrodes). Each electrode was 0.5 mm in diameter with a center-to-center spacing of 2 mm. For patients YAY, YBG and YBH, the research electrodes consisted of 16 electrodes. Each electrode was 0.5 mm in diameter with a center-to-center spacing of 4 mm or 6 mm. For patient BAA, the stimulated electrodes were located on two separate silastic strips. Each strip contained 4 electrodes. Each electrodes was was 3.18 mm in diameter with a center-to-center spacing of 10 mm.

Electrode Localization and Visualization

Before surgery, T1-weighted structural magnetic resonance imaging scans were used to create cortical surface models with the FREESURFER® software suite available https://surfer.nmr.mgh.harvard.edu/ and visualized using the SUMA software described in B. D. Argall et al., "Simplified intersubject averaging on the cortical surface using SUMA", 27 *Human brain mapping* 14-27 (2006). Subjects underwent a whole-head CT after the electrode implantation surgery. The post-surgical CT scan and pre-surgical MR scan were aligned using AFNI software described in R. W. Cox, "AFNI: software for analysis and visualization of functional magnetic resonance neuroimages" 29 *Computers and biomedical research, an international journal* 162-73 (1996), and all electrode positions were marked manually on the structural MR images. Electrode positions were then projected to the nearest node on the cortical surface model using the AFNI program Surface Metrics The electrodes consist of metal discs that lay flat on the cortical surface; when rendered on the cortical surface model, it can be difficult to see electrodes that are oriented with their edge towards the viewer because of the orientation of the cortical surface. Therefore, for visualization in this application, each electrode is rendered with the entire top surface of the electrode facing the viewer.

Overview of Procedures

Epileptic subjects were hospitalized in the epilepsy-monitoring unit for 4 to 14 days after electrode implantation. During all experiments, the patients remained seated comfortably in their hospital bed. A ground pad was adhered to the patient's thigh, and all electrical stimulation was monopolar. Electrical stimulation currents were generated using a 16-channel system (AlphaLab SnR, Alpha Omega, Alpharetta, Ga.) controlled by custom code written in MATLAB® software (Version 2013b, The MathWorks Inc., Natick, Mass.). For all patients included in the study, the epilepsy seizure focus was determined to be distant from visual cortex.

Blind subject BAA acquired blindness at age 27 and had minimal residual light perception. As a component of an early feasibility study for the development of a visual cortical prosthetic, BAA underwent surgical implantation of a neurostimulator normally used to treat epilepsy (RNS® System, Neuropace, MountainView, Calif.). Subject BAA was tested as an outpatient.

Screening to Determine Responsive Electrodes

Applicant first screened all electrodes implanted on visual cortex to identify responsive electrodes, i.e., those that produced a phosphene when electrical stimulation was delivered. In each trial, patients verbally reported whether they experienced a localized, brief, visual percept similar to a flash of light. During each trial, an auditory warning tone cued the patients to fixate visual crosshairs. This was followed by a second tone that indicated the beginning of the electrical stimulation period. Electrical stimulation consisted of a train of biphasic pulses (−/+), with 0.1 ms pulse duration per phase, delivered at a frequency of 200 Hz, with an overall stimulus train duration of 200 or 300 ms. Currents tested ranged from 0.3-4.0 mA resulting in a total charge delivered of 1.2-24 µC per trial. For each electrode, trials were initiated with a low current (0.3-1.0 mA) that gradually increased on successive trials until the patient reported a phosphene. If no phosphene was obtained with a maximum current of 4 mA, then the site was considered unresponsive.

Quantitative Phosphene Mapping Using Electrical Stimulation

To quantify phosphene locations, additional experiments were performed on each of the electrodes identified in the screening stage. The patient fixated visual crosshairs and electrical stimulation was delivered to a single electrode using the parameters that elicited a phosphene for that electrode in the screening stage. The patient drew the outline of the phosphene on a touchscreen. Multiple trials were typically conducted. On the first trial, the subject was instructed to draw the shape as accurately as possible. On subsequent trials, the patient adjusted the size and location of the phosphene using a custom designed graphical user interface so that it matched the phosphene as precisely as possible. For patient YBH, phosphenes were drawn with a pen and paper instead of a touchscreen. The patient inspected the drawing following the trial. If it did not match the percept, an additional trial was performed and a new drawing created. The paper drawings were digitized using a flatbed scanner. Phosphene drawings for each electrode (touchscreen or pen and paper) were fit with an ellipse for quantification and display. Blind subject BAA was instructed to touch (and attend to) a small VELCRO® hook-and-loop fastener square placed on the screen of an APPLE® IPAD PRO® tablet. Subject BAA traced the outline of the phosphene percept in the appropriate location on the screen of the IPAD PRO® tablet.

Receptive Field Mapping Using Visual Stimuli

For sighted patients YBN and YBH, receptive field mapping was performed to measure the visual responses of each electrode. Patients viewed an LCD screen located approximately 57 cm in front of them. Small black-and-white flashing checkerboards were presented at different locations on the screen that varied randomly from interval to interval (checkerboard duration 167 ms, blank interval of 167 ms between different locations). To ensure fixation, patients performed a letter detection task at the fixation point. A 128-channel CEREBUS™ amplifier (Blackrock Microsystems, Salt Lake City, Utah) was used to record from the subdural electrodes. An inactive intracranial electrode implanted facing the skull was used as a reference for recording. Signals were amplified, filtered (low-pass: 500 Hz, Butterworth filter with order 4; high-pass: 0.3 Hz, Butterworth filter with order 1) and digitized at 2 kHz.

Stimulation Paradigms for Studying Form Vision

To examine form vision, Applicant stimulated multiple electrodes in sequence. Each electrode was stimulated for an identical duration, with a short gap between successive electrodes during which there was no stimulation. For all electrodes, the stimulation frequency was 200 Hz and the pulse width per phase was 100 µS. The current amplitude for each electrode was held constant, and was the same used amplitude use for phosphene mapping of individual electrodes (equal to the minimum current that reliably produced a phosphene during the screening stage).

In patient YBN, the current range across the stimulated electrodes was 1.2 mA to 1.5 mA. Each electrode was stimulated for a duration of 50 ms with a no-stimulation interval between stimulation of successive electrodes of 50 ms. In patient YAY, the current range was 0.7-1.5 mA (duration 200 ms, interval 125 ms). In patient BAA, the current was 2 mA for each electrode (duration 200 ms, interval 2000 ms due to constraints imposed by the electrode control hardware and software). In patient YBH, the current range was 2-3 mA (duration 50 ms, no interval between electrodes since all electrodes were stimulated simultaneously).

In patient YBG, the technique of current steering was tested. "Virtual electrodes" were created by concurrently stimulating two adjacent electrodes. A sample stimulation pattern would consist of electrode 1 stimulation at full (100%) current; followed by electrode 1 stimulation at 75% current and electrode 2 stimulation at 25% current, creating a virtual electrode near to electrode 1; followed by electrode 1 stimulation at 50% current and electrode 2 stimulation at 50% current, creating a virtual electrode midway between electrodes 1 and 2; followed by electrode 1 stimulation at 25% and electrode 2 stimulation at 75%, creating a virtual electrode near to electrode 2; followed by electrode 2 stimulation at 100% current. Four real electrodes were used and three virtual electrodes were created between each pair of real electrodes (nine virtual electrodes total) for a total of 13 real and virtual electrodes. The current range across the stimulated electrodes was 1.5 mA to 2.0 mA, with stimulation duration 50 ms and inter-electrode interval 50 ms, resulting in a total sequence duration of 1.3 seconds to traverse all 13 electrodes.

Behavioral Tests in Subjects with Implanted Electrodes

To assess the subjects' ability to make perceptual discriminations between different electrical stimulation sequences, Applicant used a forced-choice discrimination task. Before discrimination testing, the subjects drew the perceived pattern on the touchscreen several times and they were instructed to associate a particular letter or grapheme with each stimulation sequence. During each trial of the discrimination task, a single sequence was presented while the subject fixated, or attended to, a defined place on the touchscreen, and then the subjects gave a verbal report to indicate which of the sequences they had perceived. Sequences were presented in pseudo-random order.

In the blind subject, Applicant also used a multidimensional scaling (MDS) analysis to assess the reliability of differences between the graphemes drawn by the blind subject as a result of different electrical stimulation sequences. One of 7 stimulation sequences was presented on each trial corresponding to one of 7 shapes or graphemes (G, N, R, U, V, W, Z). Each shape was repeated 4 times for a total of 28 trials. For each trial, the drawing made by the subject on the touchscreen was converted into an ordered set of hundreds of evenly spaced circles usiNG ADOBE ILLUSTRATOR® software. The x and y location of the center of each circle, and hence each point in the original drawing, was then obtained using the regionprops ( ) function in MATLAB® software. So as to have an equal number of points for each drawing, the list of coordinates corresponding to each trial was resampled to obtain exactly 100 points. A correlation matrix 28×28 in size was created by obtaining the correlation between the ordered list of x, y points from each trial, and the ordered list of points from every other trial, using the corr2( ) function in MATLAB® software. The correlation matrix was used as input to MATLAB® code that performed the MDS analysis.

Behavioral Tests in Subjects without Implanted Electrodes

Applicant created simulated phosphene displays to examine the efficacy of different stimulation paradigms (FIG. 13). 78 different displays, consisting of MP4 videos, were created: 26 letters times three stimulation paradigms (static, dynamic, dynamic+current steering).

Dynamic trajectories were simulated by activating electrodes in a sequence similar to that used when hand printing a letter; for instance, an H is drawn in three line-segments consisting of the first vertical (I) followed by the transverse element (-) followed by the second vertical (I-I). For dynamic paradigms, drawing more complex letters takes more time than simpler letters. To equate time of presentation across paradigms, the static version of a letter was presented on screen for the same amount of time as the dynamic versions of the letter.

The dynamic and dynamic+current steering presentation times were equated by presenting two identical frames in sequences (equivalent to sequential stimulation of the same electrode) for the dynamic paradigm. For instance, if the letter form consisted of stimulation of electrode 1 followed by electrode 2 followed by electrode 3, the simulated phosphene produced by each electrode would be displayed for 2 video frames in the dynamic paradigm for a total of 6 frames, while in the dynamic+current steering paradigm the same letter video would display the simulated phosphene from electrode 1 for 1 frame, followed by a simulated phosphene intermediate between electrodes 1 and 2 for 1 frame, and so on, for a total of 6 frames and equal display time.

The displays were created using a model based on the phosphenes reported by human participants with electrodes implanted in visual cortex. First, the model predicts the spread of cortical activity based on electrical current using a sigmoidal function. Second, the model predicts cortical magnification factor at the electrode location. Third, the diameter of cortex activated by electrical stimulation is multiplied by the inverse magnification factor to predict phosphene size. The base grid for the phosphene displays consisted of a three-by-three grid of 0.5 mm electrodes with the most-foveal electrode placed at 10 degrees of eccentricity with stimulation current of 1.5 mA. Dynamic current steering was implemented by creating a single virtual electrode between each pair of real electrodes, resulting in an inter-electrode distance of 2 mm for real electrodes and 1 mm for the virtual electrodes.

Participants were recruited using the AMAZON MECHANICAL TURK® platform; previous studies have demonstrated comparable results for in-person testing in the laboratory environment and AMAZON MECHANICAL TURK® platform. Participants were instructed to view each stimulus display and entered the upper-case letter that best matched their percept, and to guess if they were unsure. Each participant viewed each letter only once to prevent any effects of letter learning (for instance, seeing a current steering "F" might make it easier to recognize a later "F" presented without current steering). Because each participant viewed each letter only once, participants were randomly assigned to one of three counter-balancing groups. Each group saw one-third of the letters presented with each stimulation paradigm, with the assignment of letters to stimulation paradigm varied across group so that each letter was presented a similar number of times in each stimulation paradigm. To model the effects of the experimental manipulations on McGurk prevalence, generalized linear mixed effects (GLMM) models were constructed in the R programming language (using function glmer, with family set to binomial) with the lme4 package.

Results

Figure 10:
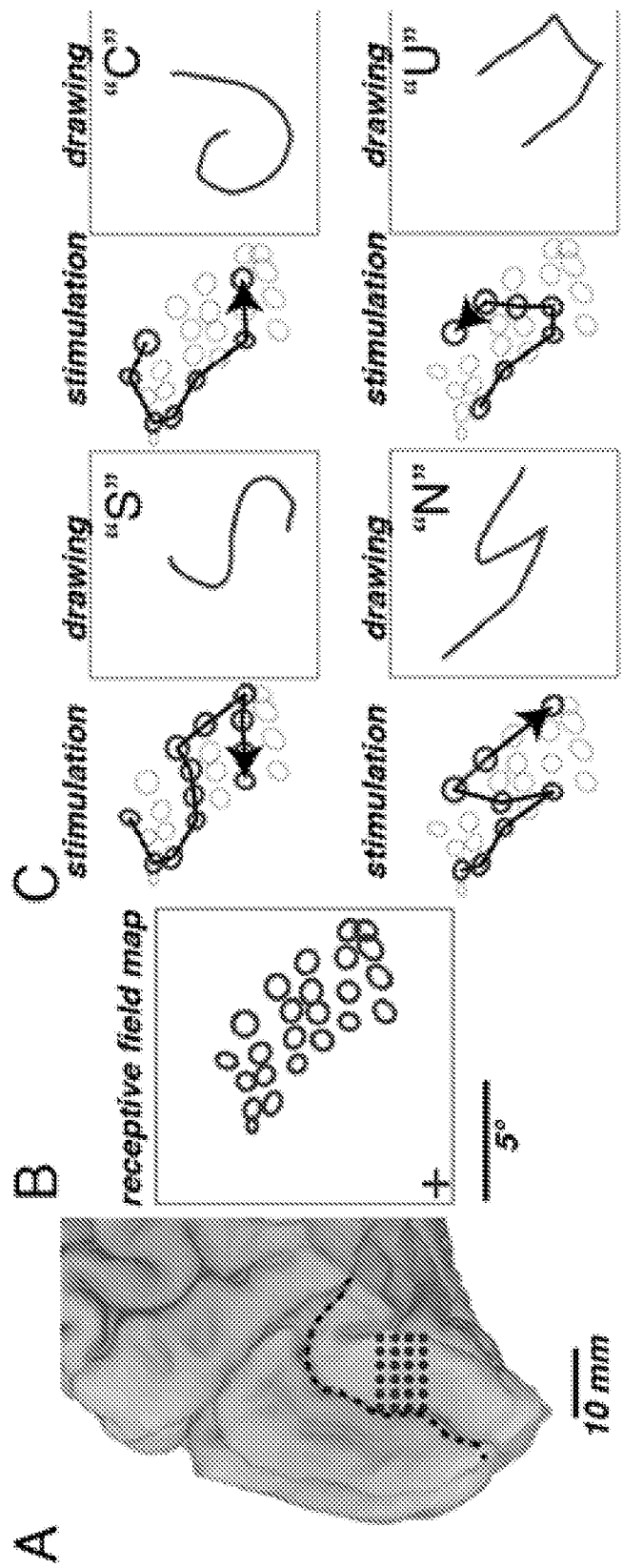
FIG. 10 depicts dynamic current steering guided by visual receptive field mapping. Panel (A) provides a medial view of the left occipital lobe of a sighted patient. Circles show the 24 electrodes contained in a grid implanted inferior to the calcarine sulcus (dashed line). In Panel (B), to generate receptive field maps, the patient fixated while mapping stimuli were presented. The circles show the location of the receptive field centers for each electrode. In Panel (C), dynamic current steering of selected electrodes was used to generate four different artificial percepts. For each percept, left panel shows the stimulated electrodes (bold circles) and direction of temporal sequence of stimulation (arrow). The right panel shows the patient's drawing of the artificial visual percept and verbal label.

To explore the utility of dynamic current steering in visual cortex, Applicant began by studying sighted patients temporarily implanted with intracranial electrodes as part of clinical monitoring for epilepsy surgery. Novel arrays of custom research electrodes were implanted in the unused space between standard clinical electrodes (clinical monitoring continued uninterrupted during all research procedures). As shown in FIG. 10, Panel A, one such array consisted of 24 electrodes (6×4) implanted on the medial face of the occipital lobe in a patient identified by the anonymized subject code YBN.

Because the patient was sighted, Applicant used receptive field mapping techniques to identify the regions of the visual field encoded by the cortex underlying each electrode. As expected from the retinotopic organization of visual cortex, there was an orderly organization to these receptive fields (FIG. 10, Panel B). All were located in the upper-right visual field, corresponding to the anatomical location of the electrode array inferior to the calcarine sulcus in the left hemisphere, and more anterior electrodes were associated with more peripheral locations in the visual field.

Using the mapped receptive fields, Applicant designed dynamic trajectories of patterned stimulation corresponding to four different letter forms. Successive electrodes in each trajectory were stimulated with small amounts of current (~1 mA) at high frequency (~200 Hz) in rapid temporal sequence (50 ms per electrode). Without any training, the patient was able to make use of the visual percepts created by dynamic current steering and reproduce them on a touchscreen.

As shown in FIG. 10, Panel C, there was a striking correspondence between the predicted and actual letter shape percepts. Applicant tested the subject's ability to identify different stimulation trajectories using a four-alternative forced-choice task. Fifteen of twenty-three presentations were accurately identified, significantly better than chance (66% vs. 25%, p=$10^{-4}$). Similar high accuracy was observed in another patient (subject code YBG) tested with three different stimulation trajectories (77% vs. 33%, p=$10^{-6}$ from binomial distribution).

Figure 11:
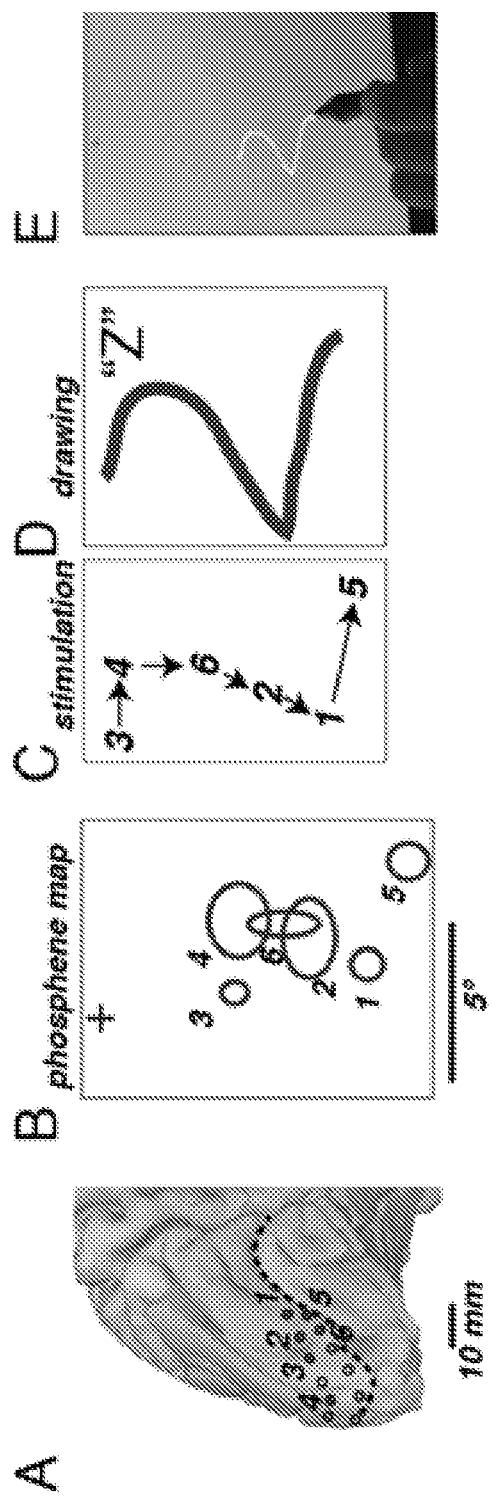
FIG. 11 depicts dynamic current steering guided by phosphene mapping according to an embodiment of the invention. Panel (A) depicts a medial view of the left occipital lobe of a sighted patient. Numbered circles show six electrodes implanted over the calcarine sulcus (dashed line) that, when stimulated, created a visual percept. Open circles show electrodes that did not create a visual percept when stimulated. In Panel (B), the patient fixated while electrical stimulation was delivered to one electrode at a time. The patient drew each phosphene on a touchscreen (bold ellipses, numbered by the corresponding electrode). In Panel (C), the phosphene map was used to design a stimulation trajectory to produce the artificial percept of the letter "Z". The black arrows show the temporal sequence of stimulated electrodes. In Panel (D), the patient drew the artificial percept on the touchscreen. Panel (E) depicts a still frame from a video of the patient drawing.

In blind patients, it is not possible to use visual stimuli to map receptive fields in order to design dynamic stimulation trajectories. Therefore, in sighted patient YAY (FIG. 11), Applicant tested a different approach in which electrodes were stimulated individually and the patient drew the resulting phosphene on a touch screen. This "phosphene map" allowed for the identification of the visual field region represented by the cortex underlying each electrode (FIG. 11, Panel B). As expected from the location of the electrodes on the upper bank of the calcarine cortex in the left hemisphere, all phosphenes were in the lower right visual field, with more anterior electrodes producing phosphenes at greater eccentricity. The phosphene map was used to design a dynamic current steering trajectory in the shape of the letter 'Z' (FIG. 11, Panel C). When this stimulation pattern was delivered, the patient was immediately able to accurately reproduce the pattern without any training (FIG. 11, Panel D).

Figure 12:
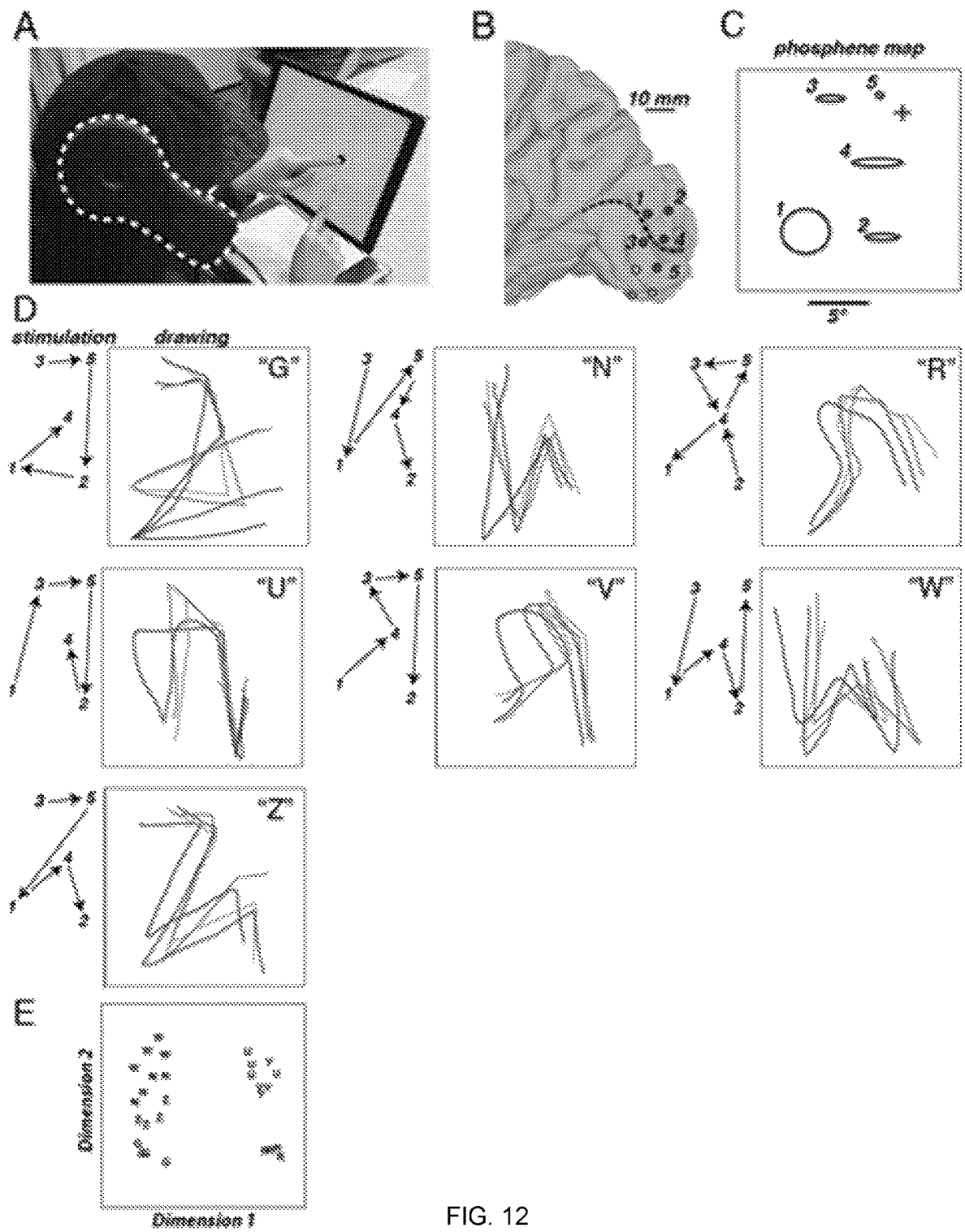
FIG. 12 depicts dynamic stimulation tested in a blind participant. In Panel (A), the wireless transmitter (dashed white line) was affixed to a cap worn by the participant. The participant placed the index figure of the left hand on a tactile fixation point (black circle) and used the index finger of the right hand to trace the artificial visual percept on the touch screen. Panel (B) depicts a medial view of a surface model of the participant's right occipital lobe. The dashed line shows calcarine sulcus; circles show electrode locations. Numbered and filled electrodes were used to create stimulation patterns; open circles show unused electrodes. In Panel (C), shapes show patient drawing of phosphenes created by stimulation of individual electrodes with numbers corresponding to electrodes in Panel (B). Crosshairs show the location of the tactile fixation point. In Panel (D), seven different letter-like shapes created by seven different dynamic stimulation patterns. The left panel for each shape shows temporal sequence of stimulation (electrodes indicated by numbers connected by black arrows). The right panel for each shape shows patient drawings to different stimulation patterns. Each line illustrates a separate trial (randomly interleaved), colored in different shades of blue for visibility. The letter shows the patient mnemonic for the pattern ("Z"; backwards "N"; backwards "R"; upside-down "U"; upside-down "V"; "W"; "Z"). Panel (E) depicts quantification of the drawings produced by the participant for each trial of each stimulation pattern using multidimensional scaling analysis of the pattern drawings. Each letter corresponds to a single trial of the corresponding stimulation pattern.

In order to investigate the feasibility of wireless stimulation of visual cortex, a blind individual underwent surgical implantation of a neurostimulator normally used to treat epilepsy (RNS® System, NeuroPace, Inc., Mountain View, Calif.) controlled through a wireless transmitter (FIG. 12). Five of the electrodes produced phosphenes when electrically stimulated, and phosphene mapping revealed two phosphenes located in the upper visual field and three phosphenes located in the lower visual field.

Seven different dynamic stimulation trajectories were designed to produce letter-like percepts. Without instruction, the blind patient was able to reproduce letter-like shapes that corresponded to the different trajectories (FIG. 12, Panel D). To assess reliability, the patient was stimulated repeatedly with each of the seven stimulation trajectories (randomly interleaved), drawing the perceived pattern following each trial. The resulting drawings were quantized, correlated, and rendered with multidimensional scaling analysis (FIG. 12, Panel E). Repetitions of the same letter-like shape clustered together, while different shapes were centered on different regions of the representational space, demonstrating that the artificial percepts were both distinct and reliable. To further quantify performance, the patient performed a forced-choice discrimination on five of the patterns. Fourteen of fifteen pattern presentations were accurately identified, much higher than expected by chance (93% vs. 20%, p=$10^{-8}$).

The limited number of patients and the limited amount of experimental time available within each patient precluded a thorough comparison between stimulation paradigms. To make these comparisons, Applicant adopted the approach of "simulated prosthetic vision" in which healthy controls view display that simulate phosphenes produced in patients with implanted electrodes. Applicant created simulated phospene displays that contained single letters created with one of three stimulation paradigms (FIG. 13).

The conventional stimulation paradigm was simulated by creating a static display of the phosphenes pattern that would be created by simultaneously stimulating electrodes in the shape of a letter using Applicant's model of current spread in visual cortex. The dynamic stimulation paradigm for each letter was created by sequentially stimulating the same electrodes used for the static display for that letter, transformed by the model. The dynamic current steering display was created by creating additional virtual electrodes located midway between the real electrodes, and sequentially stimulating the real and virtual electrodes. Simulated phosphene displays were created for each of the 26 letters in the English alphabet using the three stimulation paradigms.

Sixty-seven healthy sighted controls viewed the displays and attempted to identify each letter. Each letter was presented only once to each participant (randomly selected from one of the three stimulation paradigm) in order to minimize learning, and presentation time was equated across stimulation paradigms.

Figure 13:
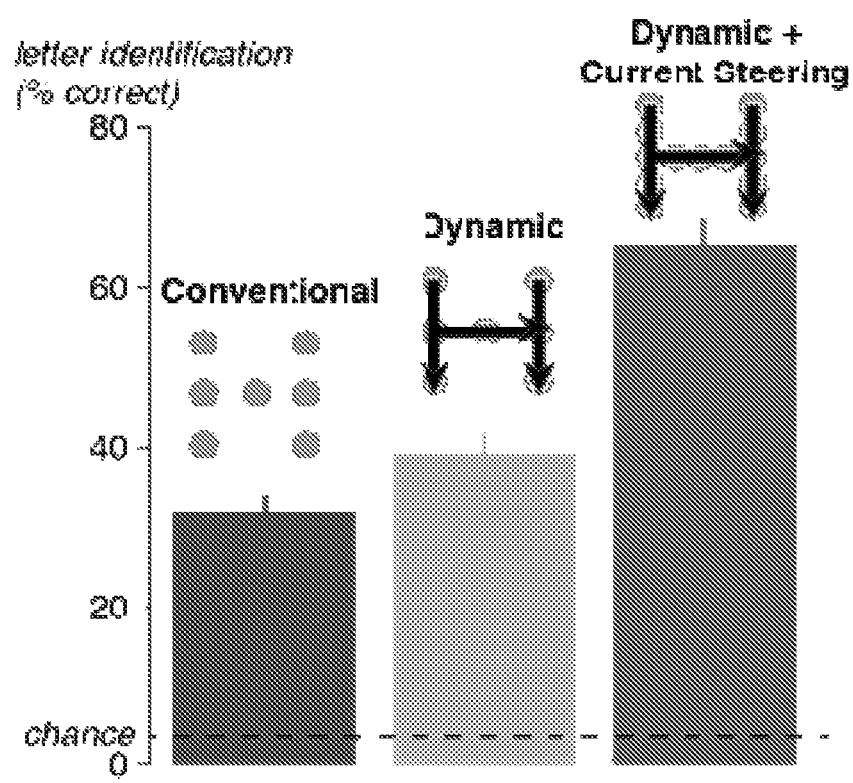
FIG. 13 depicts a comparison of different stimulation paradigms. Healthy sighted controls (n=67) viewed simulated phosphene displays and attempted to identify the letter in each display. Three types of displays were shown: displays that simulated the conventional stimulation paradigm, consisting of simultaneous stimulation of phosphenes in the shape of a letter; displays that simulated dynamic stimulation, consisting of sequential stimulation of electrodes in the shape of a letter; and displays that simulated dynamic stimulation with current steering, consisting of sequential stimulation of real electrodes and virtual electrodes located midway between the real electrodes. The three bars show the accuracy of letter identification for each display type. Error bars show the standard error of the mean across participants. Dashed line shows chance rate of 3.8%.

As shown in FIG. 13, letter identification was greater than the chance rate of 4% for the static paradigm (32%), but was higher for the dynamic paradigm (39%) and most accurate for dynamic+current steering (65%). Applicant created a linear mixed-effects model using letter and participant as random factors (because some letters might be harder or easier to recognize, and some participants might be better or worse at the task) and stimulation paradigm as a fixed effect. The model demonstrated a significant effect of paradigm, $F(2, 1650)=93.6$, p=$10^{-16}$. Post-hoc paired t-tests showed that dynamic was significantly greater than static, $t(66)=2.49$, p=0.015 and dynamic+current steering was significantly greater than both static, $t(66)=9.69$, p=$10^{-14}$, and dynamic, $t(66)=8.50$, p=$10^{-12}$.

Dynamic current steering may be more effective than static stimulation because it taps into cortical mechanisms for processing visual motion. In particular, visual motion is perceived for visual stimuli presented without a smooth trajectory, a phenomenon known as apparent motion. Dynamic current steering evokes cortical activity over a time scale (50-100 ms) similar to that which produces apparent motion with real visual stimuli. Dynamic stimulation could activate the same visual motion areas that process apparent motion and related motion phenomena, allowing for creation of a more-or-less natural percept. As reported by the subjects, a moving phosphene tracing a form is comparable to a real visual motion stimulus, such as a firefly viewed on a dark night.

The conventional static stimulation paradigm may be ineffective because it evokes patterns of activity very different from those produces by natural visual forms. Natural visual stimuli evoke activity in small populations of tuned neurons (for instance, a "T" presented at the center of gaze will activate foveal neurons in visual cortex selective for vertical and horizontal orientations but not other orientations). Electrical stimulation activates all neurons, regardless of their selectivity, instead of the isolated activity in neurons representing specific orientations that may be a precondition for activating higher cortical regions that are needed for perceiving complex shapes. Furthermore, stimulating adjacent electrodes may activate a large region of cortex that is perceived as a large, incoherent "blob" rather than discrete phosphenes.

Like natural vision, dynamic current steering allows the outline of a novel shape to be conveyed through a stimulation trajectory. The extra information that can be conveyed using a stimulation trajectory means that even a limited set of electrodes can be used to draw many different patterns.

Due to the retinotopic organization of visual cortex, phosphenes move as the eyes and head move. For instance, an electrode implanted on the superior medial wall of the right occipital lobe will produce a phosphene that is always to the left and below the fixation location, moving as the subject fixates different locations. This means that eye trackers should be incorporated into visual cortical protheses whether they use static or dynamic stimulation paradigms.

In Applicant's experiments in sighted patients implanted with electrodes, each electrode in the trajectory was stimulated for 50 ms (equivalent to 10 current pulses at a stimulation rate of 200 Hz). Reducing each electrode's stimulation time to the time needed for a single current pulse (5 ms) or even less would increase the number of electrodes that could be stimulated in a given time. The countervailing factor is the sensitivity to visual cortex of rapid stimulation. If a single electrode in visual cortex is stimulated with inter-stimulation intervals of 50 ms, the percept of a blinking or flashing phosphene is generated; reducing the interval to 25 ms results in the percept of a single, unchanging phosphene. Because a no-stimulation period of 25 ms is imperceptible, it is also possible that a stimulation time of 25 ms (or shorter) would be imperceptible, although there may be an asymmetry between onset and offset detection. Systematically measuring the quality of the percept while varying the current level and duration of electrical stimulation would allow for determination of the parameters needed for dynamic current steering to deliver visual forms as rapidly as possible; these parameters could be different for each participant, requiring a brief "tuning session" before use.

Applicant studied patients with electrodes implanted on the surface of cortex. Compared with penetrating electrodes, surface electrodes have the advantage of not damaging the neural tissue, but the disadvantage of stimulating more neurons. It is possible that with penetrating electrodes, the phosphenes created with static stimulation would be smaller and more likely to be individually controllable as "pixels" in a visual display.

In addition to its ability to convey arbitrary forms, dynamic current steering offers the advantage over static stimulation of delivering much less electrical current to cortical tissue. In the conventional static paradigm, many electrodes are concurrently stimulated, requiring substantial instantaneous power and the possibility of induction of epileptic seizures through synchronized activation. In contrast, in dynamic current steering only a small number of electrodes are concurrently stimulated (two electrodes at a time in Applicant's experiments), minimizing instantaneous power requirements. Considering other neural features, such as ongoing oscillations in visual cortex could allow further reductions in the amount of current required for dynamic current steering.

Advances in technology, including electrical stimulation with high-density grids of electrodes placed on the cortical surface or penetrating into the cortex and non-electrical stimulation with optogenetic, magnetothermal, or focused ultrasound techniques promise dramatic increases in our ability to stimulate human cortex. As a general-purpose stimulation paradigm, dynamic current steering can be used in combination with any of these technologies to restore useful visual function to blind patients.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A computer-implemented method of conveying a visual image to a blind subject fitted with a visual prosthesis, the computer-implemented method comprising:
   mapping a representation of a visual image onto a two-dimensional array of points having a resolution greater than or equal to an electrode resolution of the visual prosthesis;
   identifying one or more continuous paths along the mapped representation; and
   controlling the visual prosthesis to sequentially actuate electrodes along the one or more paths.

2. The computer-implemented method of claim 1, wherein:
   the resolution of the two-dimensional array of points is greater than the electrode resolution of the visual prosthesis; and
   the controlling step further comprises simultaneously actuating electrodes to localize a signal to a spatial point intermediate to the simultaneously actuated electrodes.

3. The computer-implemented method of claim 2, wherein the simultaneously actuated electrodes receive identical current levels and spatial location of the percept is about halfway between the electrodes.

4. The computer-implemented method of claim 2, wherein the simultaneously actuated electrodes receive different current levels and distances between spatial location of the percept and the electrodes are proportional to a ratio of current levels applied to the electrodes.

5. The computer-implemented method of claim 1, wherein the visual prosthesis is controlled to sequentially actuate the plurality of electrodes at a rate between about 2 times per second and 100 times per second.

6. The computer-implemented method of claim 1, wherein the electrodes are actuated for a duration between about 10 ms and about 500 ms.

7. The computer-implemented method of claim 1, wherein the controlling step further comprises applying an interstimulation gap between each sequential actuation.

8. The computer-implemented method of claim 7, wherein the interstimulation gap is between about 0 ms and about 100 ms.

9. The computer-implemented method of claim 1, wherein the representation includes one or more graphemes.

10. The computer-implemented method of claim 1, wherein the representation of the visual image was derived from a video image capture.

11. A system comprising:
a visual prosthesis comprising multiple electrodes; and
an imaging processing device in communication with the visual prosthesis, the imaging processing device programmed to receive an image and perform the method of claim 1.

12. The system of claim 11, wherein the visual prosthesis is selected from the group consisting of: a visual cortical prosthesis and a retinal prosthesis.

* * * * *